(12) United States Patent
Aebi et al.

(10) Patent No.: US 6,482,233 B1
(45) Date of Patent: *Nov. 19, 2002

(54) PROSTHETIC INTERBODY SPACER

(75) Inventors: Max Aebi, Montreal (CA); John S. Thalgott, Las Vegas, NV (US); Inga Häfeli, Wangen (CH)

(73) Assignee: Synthes(U.S.A.), Paoli, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 266 days.

(21) Appl. No.: 09/238,168

(22) Filed: Jan. 28, 1999

(Under 37 CFR 1.47)

Related U.S. Application Data
(60) Provisional application No. 60/072,972, filed on Jan. 29, 1998.

(51) Int. Cl.[7] .................................................. A61F 2/44
(52) U.S. Cl. .................................................. 623/17.11
(58) Field of Search .......................... 623/17.11, 17.16, 623/17; 606/61

(56) References Cited

U.S. PATENT DOCUMENTS

| | | | |
|---|---|---|---|
| 2,677,369 A | 5/1954 | Knowles | 128/92 |
| 3,848,601 A | 11/1974 | Ma et al. | 128/305 |
| 3,867,728 A | 2/1975 | Stubstad et al. | 3/1 |
| 4,309,777 A | 1/1982 | Patil | 3/1.91 |
| 4,349,921 A | 9/1982 | Kuntz | 3/1 |
| 4,401,112 A | 8/1983 | Rezaian | 128/92 |
| 4,479,491 A | 10/1984 | Martin | 128/92 |
| 4,501,269 A | 2/1985 | Bagby | 128/92 |
| 4,553,273 A | 11/1985 | Wu | 623/18 |
| 4,554,914 A | 11/1985 | Kapp et al. | 128/92 |
| 4,636,217 A | 1/1987 | Ogilvie et al. | 623/17 |
| 4,655,777 A | 4/1987 | Dunn et al. | 623/16 |
| 4,714,469 A | 12/1987 | Kenna | 623/17 |
| 4,743,256 A | 5/1988 | Brantigan | 623/17 |
| 4,759,766 A | 7/1988 | Buettner-Janz et al. | 623/17 |
| 4,834,757 A | 5/1989 | Brantigan | 623/17 |
| 4,863,476 A | 9/1989 | Shepperd | 623/17 |
| 4,863,477 A | 9/1989 | Monson | 623/17 |
| 4,874,389 A | 10/1989 | Downey | 623/17 |
| 4,878,915 A | 11/1989 | Brantigan | 623/17 |
| 4,904,261 A | 2/1990 | Dove et al. | 623/17 |
| 4,911,718 A | 3/1990 | Lee et al. | 623/17 |

(List continued on next page.)

FOREIGN PATENT DOCUMENTS

| | | | |
|---|---|---|---|
| EP | 0 599 419 A2 | 6/1994 | |
| FR | 2 703 580 | 10/1994 | A61B/17/58 |
| WO | WO 94/04400 | 3/1994 | |
| WO | WO 94/06213 | 3/1994 | |
| WO | WO 95/08306 | 3/1995 | A61F/2/44 |

OTHER PUBLICATIONS

Ralph B. Cloward, M.D., "Vertebral Body Fusion for Ruptured Cervical Discs: Description of Instruments and Operative Technic," 98 American J. of Surgery, Nov., 1959, pp. 722–727.

(List continued on next page.)

Primary Examiner—Bruce Snow
(74) Attorney, Agent, or Firm—Pennie & Edmonds LLP (57) ABSTRACT

The present invention relates to an interbody spacer for use in replacing diseased or damaged intervertebral discs and fusing together vertebrae. The implant includes an annular base portion having an anterior end, a posterior end, and two side portions together forming a continuous outer wall, and an upper and a lower face portion extending around the outer wall. A plurality of teeth extend outwardly from the upper and lower face portions of the annular base portion. The teeth are slanted in the longitudinal direction toward the anterior end and have a generally regular V-shaped configuration in the transverse direction.

19 Claims, 3 Drawing Sheets

U.S. PATENT DOCUMENTS

| | | | |
|---|---|---|---|
| 4,917,704 A | 4/1990 | Frey et al. | 623/17 |
| 4,932,769 A | 6/1990 | Goosen | 350/626 |
| 4,936,848 A | 6/1990 | Bagby | 623/17 |
| 4,946,378 A | 8/1990 | Hirayama et al. | 623/17 |
| 4,955,908 A | 9/1990 | Frey et al. | 623/17 |
| 4,961,740 A | 10/1990 | Ray et al. | 606/61 |
| 4,997,432 A | 3/1991 | Keller | 606/61 |
| 5,002,576 A | 3/1991 | Fuhrmann et al. | 623/17 |
| 5,011,484 A | 4/1991 | Bréard | 606/61 |
| 5,015,247 A | 5/1991 | Michelson | 606/61 |
| 5,035,716 A | 7/1991 | Downey | 623/17 |
| 5,047,055 A | 9/1991 | Bao et al. | 623/17 |
| 5,055,104 A | 10/1991 | Ray | 606/61 |
| 5,067,955 A | 11/1991 | Cotrel | 606/61 |
| 5,071,437 A | 12/1991 | Steffee | 623/17 |
| 5,092,893 A | 3/1992 | Smith | 623/17 |
| 5,108,438 A | 4/1992 | Stone | 623/17 |
| 5,123,926 A | 6/1992 | Pisharodi | 623/17 |
| 5,171,281 A | 12/1992 | Parsons et al. | 623/17 |
| 5,180,381 A | 1/1993 | Aust et al. | 606/61 |
| 5,192,326 A | 3/1993 | Bao et al. | 623/17 |
| 5,192,327 A * | 3/1993 | Brantigan | 623/17 |
| 5,222,954 A | 6/1993 | Baker et al. | 606/61 |
| 5,246,458 A | 9/1993 | Graham | 623/17 |
| 5,258,043 A | 11/1993 | Stone | 623/66 |
| 5,263,953 A | 11/1993 | Bagby | 606/61 |
| 5,290,312 A | 3/1994 | Kojimoto et al. | 623/17 |
| 5,294,391 A | 3/1994 | McMillin | 264/103 |
| 5,306,307 A | 4/1994 | Senter et al. | 623/17 |
| 5,306,308 A | 4/1994 | Gross et al. | 623/17 |
| 5,306,309 A | 4/1994 | Wagner et al. | 623/17 |
| 5,306,310 A | 4/1994 | Siebels | 623/17 |
| 5,314,477 A | 5/1994 | Marnay | 623/17 |
| 5,314,478 A | 5/1994 | Oka et al. | 623/18 |
| 5,320,644 A | 6/1994 | Baumgartner | 623/17 |
| 5,370,697 A | 12/1994 | Baumgartner | 623/17 |
| 5,380,324 A | 1/1995 | Müller et al. | 606/61 |
| 5,397,364 A | 3/1995 | Kozak et al. | 623/17 |
| 5,401,269 A | 3/1995 | Büttner-Janz et al. | 623/17 |
| 5,413,602 A | 5/1995 | Metz-Stavenhagen | 623/17 |
| 5,425,772 A | 6/1995 | Brantigan | 623/17 |
| 5,429,863 A | 7/1995 | McMillin | 428/224 |
| 5,443,514 A | 8/1995 | Steffee | 623/17 |
| 5,443,515 A | 8/1995 | Cohen et al. | 623/17 |
| 5,458,638 A | 10/1995 | Kuslich et al. | 623/17 |
| 5,458,642 A | 10/1995 | Beer et al. | 623/17 |
| 5,484,437 A | 1/1996 | Michelson | 606/61 |
| 5,486,174 A | 1/1996 | Fournet-Fayard et al. | 606/61 |
| 5,486,176 A | 1/1996 | Hildebrand et al. | 606/71 |
| 5,487,743 A | 1/1996 | Laurain et al. | 606/61 |
| 5,571,189 A | 11/1996 | Kuslich | 623/17 |
| 5,571,190 A | 11/1996 | Ulrich et al. | 623/17 |
| 5,609,635 A | 3/1997 | Michelson | 623/17 |
| 5,609,637 A * | 3/1997 | Biedermann et al. | 606/69 |
| 5,645,596 A | 7/1997 | Kim et al. | 623/17 |
| 5,702,449 A * | 12/1997 | McKay | 623/17 |
| 5,713,899 A | 2/1998 | Marnay et al. | 606/61 |
| 5,861,041 A * | 1/1999 | Tienboon | 623/17 |
| 5,865,845 A * | 2/1999 | Thalgott | 623/17 |
| 5,888,227 A * | 3/1999 | Cottle | 623/17 |
| 5,989,289 A * | 11/1999 | Coates et al. | 623/17 |

OTHER PUBLICATIONS

Crock, Henry V., "Practice of Spinal Surgery," Springer–Verlag, New York, 1983, pp. 37–86.

James R. Flesch, M.D., et al. "Harrington Instrumentation and Spine Fusion for Unstable Fractures and Fracture–Dislocations of the Thoracic and Lumbar Spine," 59–A Journal of Bone & Joint Surgery, Mar. 1977, pp. 143–153.

Joseph C. Flynn, M.D., et al., "Anterior Fusion of the Lumbar Spine," 61–A Journal of Bone & Joint Surgery, Inc., Dec., 1979, pp. 1143–1150.

Kiyoshi Kaneda, M.D., et al., "Burst Fractures with Neurologic Deficits of the Thoracolumbar–Lumbar Spine: Results of Anterior Decompression and Stabilization with Anterior Instrumentation," 9 Spine, Nov./Dec. 1984, pp. 788–795.

Robert A. Robinson, M.D., et al., "The Results of Interbody Fusion of the Cervical Spine," 44–A Journal of Bone & Joint Surgery, Dec., 1962, pp 1569–1587.

Edward H. Simmons, et al., "Anterior Cervical Discectomy and Fusion—Discography: Technique and Interpretation of Results," 51–B Journal of Bone & Joint Surgery, May, 1969, pp. 225–237.

Richard N. Stauffer, M.D., et al., "Anterior Interbody Lumbar Spine Fusion," 54–A Journal of Bone & Joint Surgery, Jun., 1972, pp. 756–768.

Augustus A. White, III, M.D., et al., "Relief of Pain by Anterior Cervical–Spine Fusion for Spondylosis," 55–A Journal of Bone & Joint Surgery, Apr., 1973, pp. 525–534.

* cited by examiner

PROSTHETIC INTERBODY SPACER

CROSS-REFERENCE TO RELATED APPLICATIONS

This application claims the benefit of U.S. Provisional Application No. 60/072,972, filed on Jan. 29, 1998.

FIELD OF THE INVENTION

The present invention relates to a prosthetic interbody spacer and, in particular, to an implant for use in replacing diseased and damaged intervertebral discs and fusing vertebrae.

BACKGROUND OF THE INVENTION

Human intervertebral discs generally serve two functions, they cushion and allow movement between pairs of vertebrae. Cushioning is performed by a gel-like material, which forms the inner part of the discs. A fibrous outer layer surrounds the inner gel-like material. Discs are subjected to a great many strains and stresses and are known to deteriorate with age, injury, or disease. When discs are damaged or diseased, the mobility of the subject is often impaired and great pain may result from movement. Damaged discs may also place pressure on the spinal column, causing pain.

In order to relieve some of the pain associated with disc injury and disease, it has been known to remove the diseased or damaged disc and fuse together adjoining vertebrae. Fusion is often desirable because it serves to fix the vertebral bodies together to prevent movement and maintain the space originally occupied by the intervertebral disc. The loss of mobility associated with this is often acceptable to the patient.

One method of replacing damaged or diseased discs it to insert bone graft material and utilize metal plates and screws to hold the graft material in place until healed. Healing can take a long time period, requiring inactivity for as long as six months. Problems often arise as a result of his type of vertebral fusion, such as slippage, rejection, or failure of the implant.

Discs may also be replaced using a manufactured implant, made of a synthetic material that is biologically compatible with the body and the vertebrae. These prosthetic vertebral interbody spacing devices have been used to both replace discs and vertebrae. They have taken on a number of forms including plug-like, disc-like, and other structures.

Plug-like spacers have taken on a variety of compositions and geometries, ranging from simple blocks of material to carefully shaped implants. An example of a plug-like intervertebral spacer is shown in U.S. Pat. No. 5,263,953 to Bagby, which discloses a coil-type implant which is inserted posteriorly. Plug-like implants often require that bone matter be removed, such as through drilling, in order to allow for placement of the plugs. See, e.g., U.S. Pat. No. 5,015,247 to Michelson; U.S. Pat. No. 4,834,757 to Brantigan. The device disclosed in Bagby includes threads which help to separate the viable bone of the vertebrae from the graft bone, placed in an implant cavity which is drilled into the vertebrae.

Another group of implants are more annular or disc-like in shape. These implants also often require that bone matter be removed in order to provide proper seating on adjacent vertebrae. An example of a disc-like implant is shown in U.S. Pat. No. 5,192,327 to Brantigan et al., which teaches using flat rigid generally oval-shaped discs with ridges to bite into the vertebrae and having slots and hollow areas for packing bone graft material. The Brantigan et al. device incorporates rings which may be stacked and used to replace disc and vertebrae space and requires that adjacent vertebral endplates be prepared by flattening with a burr drill in order to provide a face which is compatible with the shape of the prosthetic.

Disc-like implants are often designed with load-bearing in mind. U.S. Pat. No. 5,397,365 to Kozak et al., the disclosure of which is incorporated herein by reference in its entirety, teaches the desirability of designing the spacer such that the load is transmitted between adjacent vertebrae at the strongest part of the vertebral body, thus avoiding cavitation of the device into the surrounding vertebral endplates with collapse of the intradiscal space and possible damage to the vertebrae itself.

Discs may be replaced using both posterior and anterior techniques. Plug-like devices are often inserted posteriorly. Larger disc-like devices may typically only be inserted anteriorly due to their larger size. The present invention relates to a device which is inserted annularly.

With disc replacement, it is desirable to provide a design which promotes bone ingrowth, thus promoting stability. Avoiding retropulsion or dislodgement is also desirable. In addition, it is advantageous to provide a properly sized and shaped implant which impacts the hard cortex rim bone of the vertebrae and spans the softer interior cancellous bone material of the vertebrae. It is also desirable to reduce the amount of preparation required to the endplates of the adjoining vertebrae and to reduce the amount of bone material removed prior to insertion of the replacement disc.

There is, therefore, a need for an improved spinal disc implant which is both readily utilized in a surgical procedure and advantageously meets the above and other objectives without undesirable side effects.

SUMMARY OF THE INVENTION

Accordingly, the present invention is directed to an interbody spacer. The spacer preferably includes an annular base portion having an anterior end, a posterior end, and two side portions together forming a continuous outer wall. The spacer also includes an upper and a lower face portion extending around the outer wall. A plurality of teeth preferably extend outwardly from the upper and lower face portions. The teeth are slanted in the longitudinal direction toward the anterior end and have a generally regular V-shaped configuration in the transverse direction.

In a preferred embodiment, the base portion is generally convex in the transverse direction. The base portion may also be wedge-shaped and concave in the longitudinal direction.

The teeth are preferably configured and dimensioned in the shape of four-sided pyramids to facilitate penetration of the end faces of vertebrae. The teeth may substantially cover the entire upper and lower faces of the base portion and are preferably aligned longitudinally and transversely in a plurality of rows. The teeth may be substantially symmetrical in the transverse direction.

The annular base portion may include an inner wall having at least one groove formed at least around a portion thereof and is wedge-shaped in order to aid in restoring normal anatomical posture. For this purpose, the base portion has a greater height at the anterior end than at the posterior end.

In a preferred embodiment, the base portion is generally oval. The oval may include at least one flattened end. The annular base portion is preferably shaped to substantially conform to an endplate of an adjoining vertebrae and is configured and dimensioned to receive a bone grafting material.

The outer wall of the base portion may include at least one groove defined therein for joining with an insertion device. The outer wall may also include at least one aperture extending therethrough for joining with an insertion device.

The implant may replace the entire disc or may be inserted into the fibrous annulus of an intervertebral disc.

BRIEF DESCRIPTION OF THE DRAWINGS

Preferred features of the present invention are disclosed in the accompanying drawings, wherein similar reference characters denote similar elements throughout the several views, and wherein.

DETAILED DESCRIPTION OF THE PREFERRED EMBODIMENTS

As used herein, anterior refers to the front end and posterior refers to the rear end. The longitudinal direction runs from the anterior end to the posterior end and the transverse direction is perpendicular to the longitudinal direction (or from side to side).

FIGS. 1–4 show a preferred embodiment of the interbody spacer or implant 10 of the present invention. The implant 10 is designed for replacement of discs between adjoining vertebrae in the spinal column. When inserted, the implant 10 restores disc height and fuses the adjoining vertebrae together. The implant 10 may be utilized to replace the entire disc or to replace only the interior of the disc, with the fibrous annulus of the disc remaining. With the latter technique, the implant 10 is inserted into the annulus to replace the removed disc material.

Figure 3:
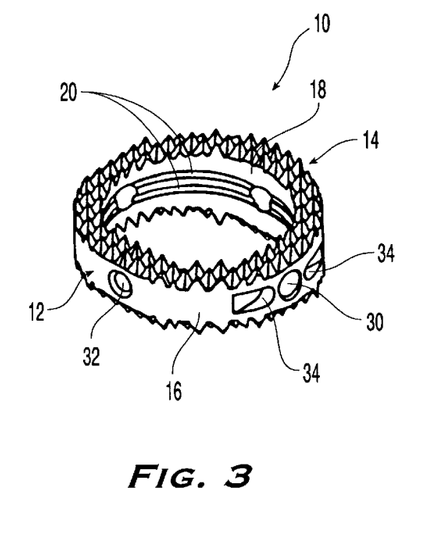
FIG. 3 is a perspective posterior view of the interbody spacer depicted in FIG. 1.
Figure 4:
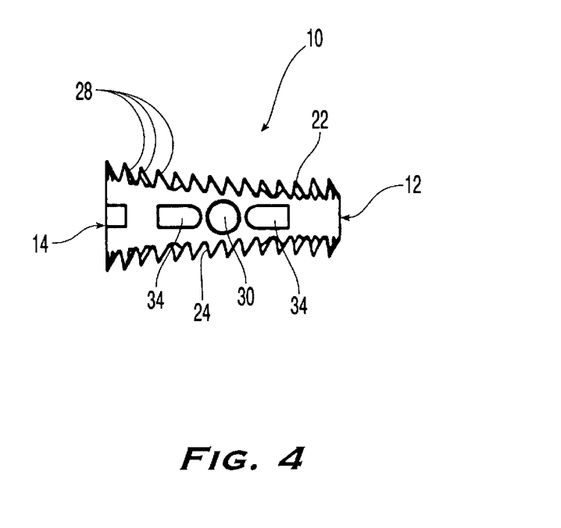
FIG. 4 is an elevated side view of the interbody spacer depicted in FIG. 1.

The implants 10 of the present invention are preferably ring or annular-shaped. FIGS. 1–4 show an embodiment of an oval-shaped implant 10. As shown in FIG. 4, implant 10 is preferably wedge-shaped, when viewed from the side (longitudinally). Wedge-shaped implants are preferred in order to restore normal anatomical alignment upon insertion. For this purpose, implant 10 has a shorter height at the posterior end 12 than at the anterior end 14. Implant 10 may be inserted anteriorly, but not posteriorly. The wedge shape is provided in order to mimic the shape of the adjoining vertebrae and to provide a lordotic profile.

Figure 1:
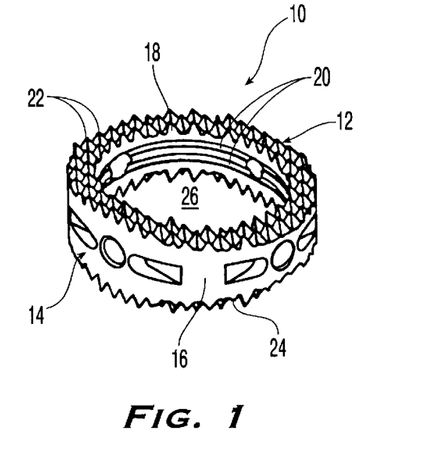
FIG. 1 is a perspective anterior end view of a preferred embodiment of the interbody spacer of the present invention.
Figure 2:
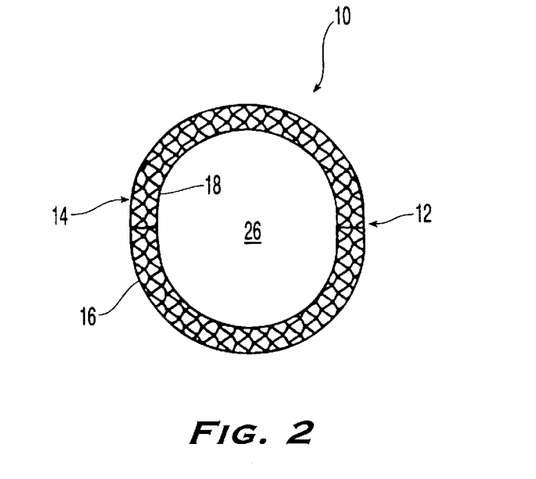
FIG. 2 is a top view of the interbody spacer depicted in FIG. 1.

Implant 10 preferably includes a smooth outer peripheral wall 16 and an inner facing wall 18. Alternatively, outer wall 16 may be roughened. Grooves 20 may extend around the interior wall 18 of the implant 10. As shown in FIGS. 1 and 3, two grooves 20 may be provided and preferably extend around the entire interior wall 18. These grooves 20 are for receiving bony ingrowth after the implant 10 is inserted between the vertebrae. Each implant 10 has a top face 22 and bottom face 24, which may be identical in configuration. An aperture 26 extends through the implant 10, with the aperture 26 being open at each face 22, 24.

The interior aperture 26 of the implant 10 may be filled with a bone graft material or a bone graft substitute prior to insertion. This bone graft material serves to create a column of bone, assisting in the fusion process. The bone graft material grows into the grooves 20 on the interior wall 18 of implant 10, as well as to the adjoining surfaces of the vertebrae. For example, Pro Osteon Implant 500 (IP500), a synthetic bone graft substitute, may be utilized in the interior aperture 26.

Figure 6:
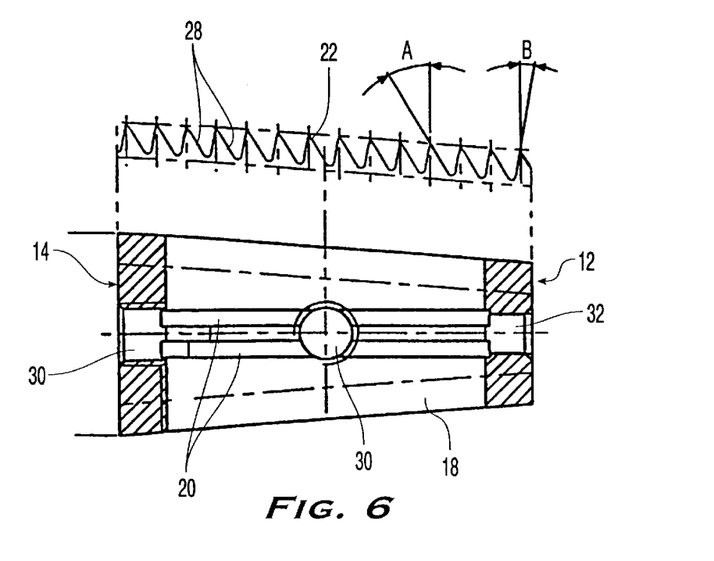
FIG. 6 is a cross-sectional side view of the interbody spacer depicted in FIG. 5 taken along line 6—6.
Figure 7:
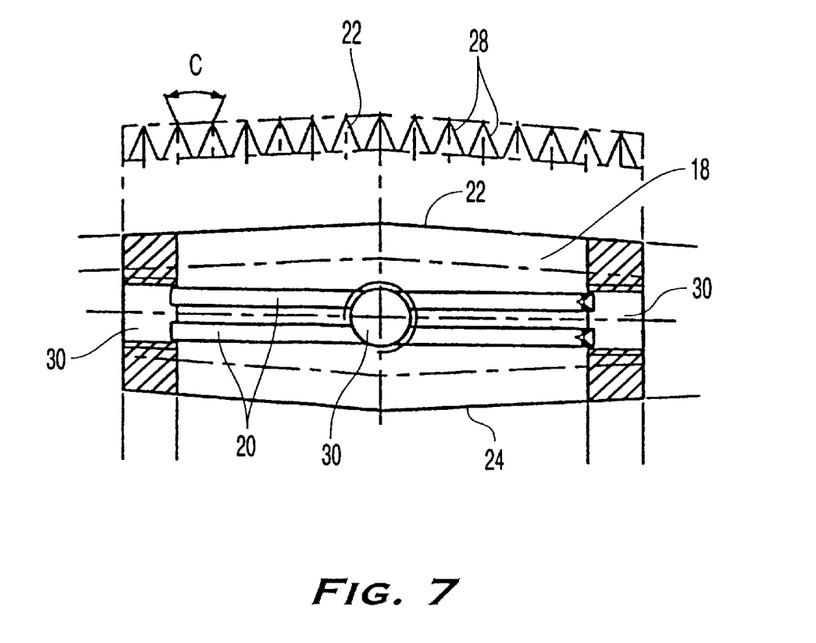
FIG. 7 is a cross-sectional end view of the interbody spacer depicted in FIG. 5 taken along line 7—7.

Each end face 22, 24 of the implant 10 preferably includes a plurality of spikes or teeth 28, as shown in FIGS. 1, 3, 4, 6, and 7. The spikes 28 are particularly configured so that in a first longitudinal direction, as shown in FIG. 6, they are arranged in a saw tooth pattern, with the spikes being slanted on one side more than on the other. The spikes are preferably slanted toward the anterior end and resemble shark teeth. In the transverse direction, as shown in FIG. 7, the spikes are arranged in a regular "V" shape, with each side of the spikes being at about the same angle as the other side. Other shapes may also be utilized.

The spikes in FIG. 6 are shown in the longitudinal direction and preferably are slanted toward the anterior end in order to allow for ease of insertion and to avoid retropulsion after insertion. The peaks of the spikes may range from about 1 mm to about 5 mm apart. In a preferred embodiment, the spikes are about 1.9 mm apart. The posterior side of each spike is preferably slanted at an angle A, which may preferably range from about 20° to about 60° relative to the vertical. In a preferred embodiment, angle A is about 30° relative to the vertical. The anterior side of each spike is preferably slanted at an angle B which may preferably range from about 0° to about 30°. In a preferred embodiment, angle B is about 10° relative to the vertical. It should be understood that these dimensions may be varied as required by size and other considerations.

The spikes in FIG. 7 are depicted in the transverse direction as being substantially V-shaped and symmetrical. Again, in a preferred embodiment, the peaks of the spikes are preferably about 2 mm apart, and, most preferably about 1.9 mm apart. The sides of the peaks are preferably at an angle C of about 45° relative to one another. It should be understood that these dimensions may also be varied as required by size and other considerations.

The spikes 28 are aligned in the lateral and longitudinal directions to form rows of spikes. Each spike 28 is positioned directly adjacent another spike 28. The spikes 28 are preferably pointed. Machining tolerances, however, may provide slightly flattened points, which is acceptable.

The spikes 28 cover the entire surface area of each face 22, 24 of implant 10. Spikes 28 in this arrangement provide rotational stability to the implant 10 and, thus, are less likely to rotate after insertion because each point of the spike 28 penetrates the opposing vertebrae. The orientation of the spikes is also designed for ease of insertion and to prevent retropulsion or dislodgement. The spikes 28 may penetrate fully into the endplates of the vertebrae or may penetrate only partially. With the latter, bony ingrowth may occur around the spikes 28 which have not fully penetrated.

Figure 5:
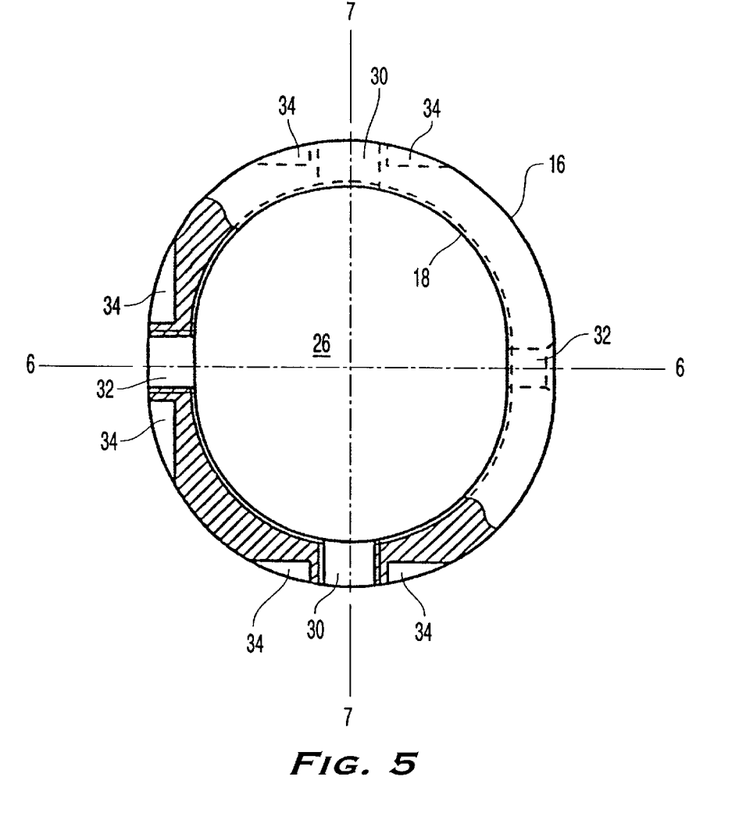
FIG. 5 is a partial cross-sectional top view of the interbody spacer depicted in FIG. 1.

As shown in FIG. 5, each implant 10 preferably includes four holes or apertures 30 placed at centrally disposed locations around the outer wall 16. The holes 30 extend through the implant 10 from the outer wall 16 to the interior wall 18 to form a passageway therebetween. The holes 30 are preferably about 2–3 mm in diameter and are sized for mating with an insertion device. As such, the size of the holes 30 is not crucial to the invention, although it is recognized that a size limitation is presented by the overall size of the implant 10.

Holes 30 preferably have screw threads for engaging with an insertion device, or mounting tool (not shown). Alternatively, the holes 32 may be provided without screw threads where the hole 32 is not for use with an insertion device. When not needed for use with an insertion device or mounting tool, a hole 32 is not required. Grooved portions 34 of the outer peripheral wall 16 may be disposed on either side of each screw thread hole 30 for association with an insertion tool.

The holes 30, 32 may be positioned at each posterior 12 and anterior 14 end, in alignment with a longitudinal axis of implant 10. A third and fourth hole 30 may be positioned transversely on implant 10. The holes 30 are preferably positioned at equal intervals around the outer wall 16 of the implant.

The implant preferably includes curved and angled face surfaces 22, 24. The faces are preferably angled to form a wedge shape in the longitudinal direction. The faces 22, 24 may also be generally concave in the longitudinal direction, as shown in FIG. 4. The inserts are preferably generally convex in the transverse direction, as shown in FIG. 7. Providing the insert with a convex and concave profile serves to more readily mate the insert with the contours of the adjoining vertebrae. By providing an implant which is shaped in this manner, less bone matter is required to be removed from the vertebrae in order to properly seat the implant 10.

Figure 8:
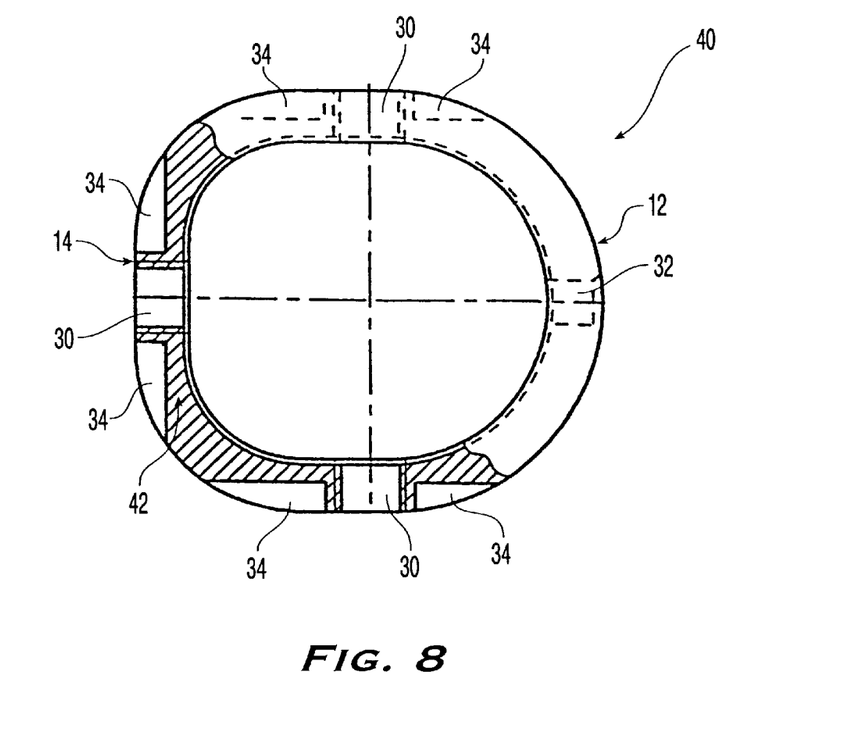
FIG. 8 is a partial cross-sectional top view of an alternative embodiment of the interbody spacer of the present invention.

FIG. 8 depicts an alternative embodiment of the present invention with an implant 40 having a flattened oval shape. The flattened portion 42 of the oval is preferably positioned at the anterior end 14 and the longest dimension is preferably the longitudinal dimension. Alternatively, other shapes may be utilized, with the goal of approximating the shape of the vertebral body endplates.

In inserting the implant of the present invention, the surgeon may excise all or only part of the diseased or damaged disc occupying the space between the adjoining vertebrae. The implant is sized and shaped to fit the disc space between the vertebrae and has a thickness sufficient to maintain this space. The implants are preferably sized such that the faces bottom on the cortex rim bone of adjacent vertebrae and span the softer interior cancellous bone. The teeth or spikes 28 pierce the adjoining endplates of the vertebrae and anchor the spacer 10 in position without requiring an additional holding means.

In preparing a site for insertion of an implant 10, a surgeon will preferably expose the interspace between the vertebrae and the iliac artery and vein are mobilized. This is done by retracting the iliac artery and vein, exposing the direct anterior aspect of the interspace. The annulus of the disc is opened with a scalpel and/or electric cautery. The disc may be removed from the superior and inferior endplates of the adjoining vertebrae using an endplate cutter, which is placed in the interval between the disc and the bony endplate.

Once the disc is removed, the lateral left and right annuli are cut and the disc is grossly debrided using curettes and rongeurs. Once the disc is debrided, the annulus may be left intact, or if anterior decompression of the disc is indicated, the annulus may be opened and the spinal canal may be opened and decompressed. Once this is completed, the disc removal phase is completed.

The endplates are then prepared using a series of curettes to remove any remaining cartilaginous disc material. Care is taken to leave as much of the bony endplate intact as possible, but the anterior lip of the vertebral body may be removed with an osteotome or high speed burr to allow anterior access for placement of the largest possible implant.

Once anterior access is obtained by removal of a small amount of the anterior lip of the vertebrae, the interspace is sized. An appropriately sized implant should fit below the anterior lip and be contained within the intervertebral space. The implant should not protrude anteriorly to the anterior rim of the intervertebral bodies as sharp edges could allow a vascular injury on either an immediate or delayed basis. The implant should be as large as possible, but if it does not seat well or is not completely contained within the intervertebral space, more disc and bone should be removed to allow more posterior positioning. Alternatively, a smaller implant may be selected.

The implant is preferably placed as parallel with the endplates as possible using an insertion instrument and is placed to create a lordotic attitude of the endplate, mimicking the normal anatomy. The implant may be introduced with an insertion device and may be finally placed using a large tamp and mallet. Alternatively, the implant may be inserted using a direct lateral retroperitoneal approach.

Implant 10 is preferably made of an inert metal substrate such as stainless steel, cobalt-chromium-molybdenum alloys, titanium or the like. Other materials are also contemplated. The implant may also be anodized if so desired. This may result in slight roughening of the outer wall 16. Alternatively, if a roughened outer wall 16 is desired, other means may be employed to roughen the surface.

Although the immediate concern leading to this disclosure was directed to the spine, anterior in approach, the described interbody spacer may be used in any joint having appropriate surrounding soft tissue. The annulus of a vertebral disc was used for illustration purposes herein and should not be construed as limited only to such applications.

It should be understood that variations and modifications within the spirit and scope of the invention, beyond those discussed herein, may occur to those skilled in the art to which the invention pertains. Accordingly, all expedient modifications readily attainable by one versed in the art from the disclosure set forth herein are to be included as further embodiments of the present invention. The scope of the present invention accordingly is to be defined as set forth in the appended claims.

What is claimed is:

1. An interbody spacer comprising:
   an annular base portion having an anterior end, a posterior end, and two side portions together forming a continuous outer wall, and an upper and a lower face portion extending around the outer wall; and
   a plurality of teeth extending outwardly from the upper and lower face portions, said teeth being slanted in the longitudinal direction toward the anterior end and having a generally regular V-shaped configuration in the transverse direction.

2. The interbody spacer of claim 1, wherein said base portion is generally convex in the transverse direction.

3. The interbody spacer of claim 2, wherein said base portion is wedge-shaped in the longitudinal direction.

4. The interbody spacer of claim 3, wherein said base portion is generally concave in the longitudinal direction.

5. The interbody spacer of claim 1, wherein said teeth are configured and dimensioned in the shape of four-sided pyramids to facilitate penetration of the end faces of vertebrae.

6. The interbody spacer of claim 1, wherein said teeth are substantially symmetrical in the transverse direction.

7. The interbody spacer of claim 1, wherein said teeth substantially cover the entire upper and lower faces of the base portion.

8. The interbody spacer of claim 7, wherein said teeth are aligned longitudinally and transversely in a plurality of rows.

9. The interbody spacer of claim 1, wherein said annular base portion includes an inner wall having at least one groove formed at least around a portion thereof.

10. The interbody spacer of claim 1, wherein said annular base portion is wedge-shaped in order to aid in restoring normal anatomical posture, with the base portion having a greater height at the anterior end than at the posterior end.

11. The interbody spacer of claim 1, wherein said annular base portion is generally oval.

12. The interbody spacer of claim 11, wherein said oval includes at least one flattened end.

13. The interbody spacer of claim 1, wherein said annular base portion is shaped to substantially conform to an endplate of an adjoining vertebrae and is configured and dimensioned to receive a bone grafting material.

14. The interbody spacer of claim 1, wherein said outer wall includes at least one groove defined therein for joining with an insertion device.

15. The interbody spacer of claim 1, wherein said outer wall includes at least one aperture extending therethrough for joining with an insertion device.

16. An interbody spacer comprising:

an annular base portion having an anterior end, a posterior end, and two side portions together forming a continuous outer wall, and an upper and lower face portion extending around the outer wall, said base portion being generally convex in the transverse direction and wedge-shaped in the longitudinal direction; and a plurality of teeth extending outwardly from the upper and lower face portions.

17. The interbody spacer of claim 16, wherein said teeth are slanted in the longitudinal direction toward the anterior end and have a generally regular V-shape in the transverse direction.

18. The interbody spacer of claim 17, wherein said teeth are substantially symmetrical in the transverse direction.

19. The interbody spacer of claim 16, wherein said teeth are configured and dimensioned in the shape of four-sided pyramids to facilitate penetration of the end faces of vertebrae.

* * * * *

UNITED STATES PATENT AND TRADEMARK OFFICE
CERTIFICATE OF CORRECTION

PATENT NO. : 6,482,233 B1
DATED : July 10, 2003
INVENTOR(S) : Max Aebi, John S. Thalgott and Inga Hafeli It is certified that error appears in the above-identified patent and that said Letters Patent is hereby corrected as shown below:

<u>Column 4,</u>
Line 22, please delete existing paragraph and replace it with the following substitute paragraph:
-- Each end face 22, 24 of the implant 10 preferably includes a plurality of spikes or teeth 28, as shown in Figs. 1, 3, 4, 6, and 7. The spikes 28 are particulary configured so that in a first longitudinal direction taken along line 6-6 in Fig. 5, as shown in Fig. 6, they are arranged in a saw tooth pattern, with the spikes being slanted on one side more than on the other. The spikes are preferably slanted toward the anterior end and resemble shark teeth. In the transverse direction taken along line 7-7 in Fig. 5, as shown in Fig. 7, the spikes are arranged in a regular "V" shape, with each side of the spikes being at about the same angle as the other side. Other shapes may also be utilized. --

<u>Column 6, line 54 through Column 7, line 2,</u>
Please delete existing claims 1-4, 9 and replace with substitute claims 1-4:
1. An interbody spacer comprising:

an annular base portion having an anterior wall, a posterior wall, and two side walls together forming a continuous outer wall, and an upper and lower face portion extending around the outer wall; and a plurality of teeth extending outwardly from the upper and lower face portions, said teeth being slanted in the longitudinal direction toward the anterior end and having a generally regular V-shaped configuration in the transverse direction, wherein the upper and lower face portions are non-planar.

2. The interbody spacer of claim 1, wherein said upper and lower face portions are generally convex in the transverse direction when viewed from the side of the anterior wall.

3. The interbody spacer of claim 2, wherein said base portion is wedge-shaped in the longitudinal direction when viewed from the side of the side walls.

4. The interbody spacer of claim 3, wherein said upper and lower face portions are generally concave in the longitudinal direction when viewed from the side of the side walls.

UNITED STATES PATENT AND TRADEMARK OFFICE
CERTIFICATE OF CORRECTION

PATENT NO. : 6,482,233 B1
DATED : July 10, 2003
INVENTOR(S) : Max Aebi, John S. Thalgott and Inga Hafeli It is certified that error appears in the above-identified patent and that said Letters Patent is hereby corrected as shown below:

Column 7,
Lines 15-17, claim 9 should read:
9. The interbody spacer of claim 1, wherein said annular base portion includes an inner surface having at least one groove formed at least around a portion thereof.

Column 8,
Lines 8-16, claim 16 should read:
16. An interbody spacer comprising:

an annular base portion having an anterior wall, a posterior wall, and two side walls together forming a continuous outer wall, and an upper and lower face portion extending around the outer wall, said upper and lower face portions being generally convex in the transverse direction when viewed from the side of the anterior wall and wedge-shaped in the longitudinal direction when viewed from the side of the side walls; and     a plurality of teeth extending outwardly from the upper and lower face portions.

Signed and Sealed this

Twenty-first Day of October, 2003

JAMES E. ROGAN
*Director of the United States Patent and Trademark Office*